(12) United States Patent
Lee et al.

(10) Patent No.: US 8,188,858 B2
(45) Date of Patent: May 29, 2012

(54) METHOD AND APPARATUS FOR COLLECTING DATA

(75) Inventors: Kwong Hyeon Lee, Yongin-si (KR); Kyung Ho Kim, Yongin-si (KR); Sang Hoon Shin, Seongnam-si (KR); Hyun Tal Hwang, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1601 days.

(21) Appl. No.: 11/372,377

(22) Filed: Mar. 10, 2006

(65) Prior Publication Data

US 2007/0055483 A1    Mar. 8, 2007

(30) Foreign Application Priority Data

Sep. 8, 2005  (KR) .................. 10-2005-0083741

(51) Int. Cl.
  *G08B 1/08* (2006.01)
(52) U.S. Cl. ............. 340/539.12; 340/572.4; 340/539.1; 340/5.8; 600/300
(58) Field of Classification Search .................. 340/5.1, 340/5.2, 5.74, 502, 539.12, 573.1, 870.01, 340/825, 539.1, 539.11, 10.1, 572.1, 572.4, 340/5.8; 600/300, 601, 607, 301
  See application file for complete search history.

(56) References Cited

U.S. PATENT DOCUMENTS

| | | | | |
|---|---|---|---|---|
| 4,460,892 A | * | 7/1984 | Bailey, Jr. | 340/555 |
| 4,628,327 A | * | 12/1986 | Anderson et al. | 346/33 ME |
| 5,335,664 A | * | 8/1994 | Nagashima | 600/508 |
| 5,377,267 A | * | 12/1994 | Suzuki et al. | 380/248 |
| 5,488,649 A | * | 1/1996 | Schellinger | 455/411 |
| 5,576,952 A | * | 11/1996 | Stutman et al. | 600/300 |
| 5,821,523 A | * | 10/1998 | Bunte et al. | 235/472.01 |
| 5,873,369 A | * | 2/1999 | Laniado et al. | 600/300 |
| 5,875,395 A | * | 2/1999 | Holmes | 455/420 |
| 5,963,149 A | * | 10/1999 | Nagura et al. | 340/933 |
| 6,147,618 A | * | 11/2000 | Halleck et al. | 340/669 |
| 6,265,963 B1 | * | 7/2001 | Wood, Jr. | 340/10.4 |
| 6,289,238 B1 | * | 9/2001 | Besson et al. | 600/509 |
| 6,315,719 B1 | | 11/2001 | Rode et al. | 600/300 |
| 6,336,900 B1 | * | 1/2002 | Alleckson et al. | 600/485 |
| 6,386,882 B1 | * | 5/2002 | Linberg | 434/262 |
| 6,551,252 B2 | * | 4/2003 | Sackner et al. | 600/536 |
| 6,611,846 B1 | * | 8/2003 | Stoodley | 707/740 |
| 6,906,625 B1 | * | 6/2005 | Taylor et al. | 340/539.13 |
| 6,922,559 B2 | * | 7/2005 | Mohammed | 455/421 |
| 6,925,324 B2 | * | 8/2005 | Shusterman | 600/509 |
| 7,171,166 B2 | * | 1/2007 | Ng et al. | 455/73 |
| 7,206,585 B2 | * | 4/2007 | Gilham et al. | 455/450 |

(Continued)

FOREIGN PATENT DOCUMENTS

JP    10-295651    11/1998

(Continued)

*Primary Examiner* — Daniel Wu
*Assistant Examiner* — Rufus Point
(74) *Attorney, Agent, or Firm* — Staas & Halsey LLP

(57) ABSTRACT

A method and apparatus for collecting data, and more particularly, a data collecting method and apparatus which automatically transmit data to a wireless data transmitting/receiving station when an amount of data stored in the data collecting apparatus is more than a predetermined first reference value. A data collecting apparatus includes: a measuring module measuring data and storing the measured data in a storage unit; and a communication module automatically transmitting the stored data to a wireless data transmitting/receiving station when the amount of data stored in the storage unit is more than a first reference value.

23 Claims, 4 Drawing Sheets

U.S. PATENT DOCUMENTS

| | | | | |
|---|---|---|---|---|
| 7,242,923 | B2* | 7/2007 | Perera et al. | 455/411 |
| 7,474,219 | B2* | 1/2009 | Richards et al. | 340/572.4 |
| 7,489,240 | B2* | 2/2009 | Soliman | 340/572.1 |
| 7,496,838 | B2* | 2/2009 | Salter et al. | 715/239 |
| 7,515,043 | B2* | 4/2009 | Welch et al. | 340/539.12 |
| 7,592,908 | B2* | 9/2009 | Zhang et al. | 340/539.13 |
| 7,639,145 | B2* | 12/2009 | Lawson et al. | 340/573.1 |
| 7,668,588 | B2* | 2/2010 | Kovacs | 600/509 |
| 2002/0007354 | A1* | 1/2002 | Deguchi | 705/418 |
| 2002/0016719 | A1* | 2/2002 | Nemeth et al. | 705/2 |
| 2002/0069211 | A1* | 6/2002 | Kondo et al. | 707/104.1 |
| 2003/0174070 | A1* | 9/2003 | Garrod et al. | 340/870.07 |
| 2004/0252012 | A1* | 12/2004 | Beenau et al. | 340/5.4 |
| 2005/0044424 | A1* | 2/2005 | Xydis | 713/201 |
| 2005/0197127 | A1* | 9/2005 | Nakasaku et al. | 455/445 |
| 2006/0109437 | A1* | 5/2006 | Kang | 355/52 |
| 2007/0195910 | A1* | 8/2007 | Shimizu | 375/299 |
| 2007/0197878 | A1* | 8/2007 | Shklarski | 600/300 |
| 2008/0224852 | A1* | 9/2008 | Dicks et al. | 340/539.12 |
| 2009/0082684 | A1* | 3/2009 | Sornmo et al. | 600/513 |

FOREIGN PATENT DOCUMENTS

| | | |
|---|---|---|
| JP | 10-302188 | 11/1998 |
| JP | 2001-067373 | 3/2001 |
| JP | 2002-051160 | 2/2002 |
| JP | 2004-13628 | 1/2004 |
| JP | 2005-157992 | 6/2005 |
| KR | 10-1998-086406 | 12/1998 |
| KR | 10-2003-0077248 | 10/2003 |
| KR | 10-2004-0049486 | 6/2004 |
| KR | 10-2004-0087870 | 10/2004 |

* cited by examiner

| IDENTIFIERS |
|---|
| 1000001 |
| 1000002 |
| ⋮ |

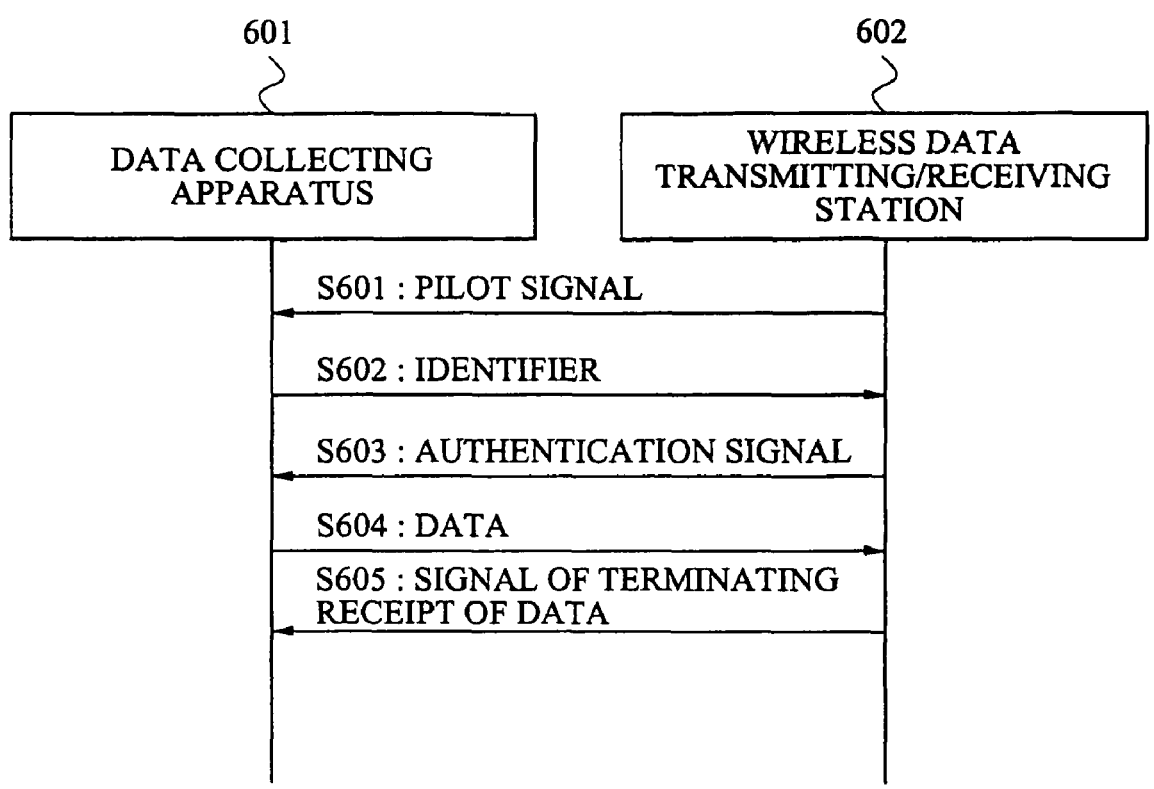

METHOD AND APPARATUS FOR COLLECTING DATA

CROSS-REFERENCE TO RELATED APPLICATION

This application claims the benefit of Korean Patent Application No. 2005-83741, filed on Sep. 8, 2005, in the Korean Intellectual Property Office, the disclosure of which is incorporated herein by reference.

BACKGROUND OF THE INVENTION

1. Field of the Invention

The present invention relates to a method and apparatus for collecting data, and more particularly, to a data collecting method and apparatus which automatically transmits data to a wireless data transmitting/receiving station when an amount of data stored in the data collecting apparatus is more than a predetermined amount.

2. Description of Related Art

Portable data measuring apparatuses collecting data have been developed for users for various purposes. These data measuring apparatuses measure various data for predetermined time, store the measured data in a predetermined storage unit, and transmit the data recorded in the storage unit to a user PC, a web server, and the like.

These data measuring apparatuses include, for example, biosignal measuring apparatuses measuring and storing a user's biosignal, digital cameras or camcorders recording pictures or moving picture data photographed by a user, and location measuring apparatuses measuring a user's location.

However, there is a constraint on the capacity of a storage unit of the data measuring apparatus. Thus, when the data measuring apparatus measures data for more than certain time and stores the measured data in a storage unit, the capacity of the storage unit easily becomes full. Accordingly, the data stored in the storage unit has to be uploaded to a database of a user PC or a web server having a larger capacity of the storage unit. This is to continue to use the data measuring apparatuses described above.

FIG. 1 is a diagram illustrating a network connection of a conventional data measuring apparatus. Referring to FIG. 1, a data measuring apparatus 101 is connected to a user PC 103 via a wired cable 102. A user controls the user PC 103 to upload data stored in a storage unit of the data measuring apparatus 101 to the user PC 103.

When the data measuring apparatus 101 is a calorie tracker measuring the amount of motion of a user, data associated with the amount of motion of the user is stored in a storage unit of the calorie tracker. When no more data can be stored in the storage unit of the calorie tracker the user connects the calorie tracker to the user PC 103 via the wired cable 102 and uploads the measured data of a predetermined time to a user terminal.

In this case, the user may control the user PC 103 to delete the uploaded data from the storage unit of the data measuring apparatus 101, so as to recover the capacity of the storage unit. Also, the user may transmit the data stored in the user PC 103 to a data center 105 via a predetermined network 104.

When the user is a patient, data associated with the amount of motion of the user may be used for the user's checkup. Accordingly, the user transmits the data stored in the user PC 103 to the data center 105.

However, to upload data stored in a storage unit of a data measuring apparatus 101 in the conventional art to a user PC 103 or a predetermined web server, a user must connect the data measuring apparatus 101 and the user PC 103 by using a cable or the like and control the user PC 103 to upload data. Also, when the user did not upload data stored in the storage unit before the available capacity ran out, storage space became unavailable to store additional data. Accordingly, there was a concern of losing data.

Also, a user had to transmit data stored in a user PC 103 to a data center 105 in order to make the data center manage data measured from the data measuring apparatuses 101.

Also, a method of making a predetermined support apparatus wirelessly transmit data stored in a data measuring apparatus 101 to a predetermined server when the data measuring apparatus 101 and the supporter were connected was suggested to solve the above inconveniences. However, in the aforementioned method, data was transmitted only when a data measuring apparatus 101 and a supporter were connected. Also, the capacity of a storage unit of the data measuring apparatus 101 was not automatically controlled.

BRIEF SUMMARY

An aspect of the present invention provides a data collecting method and apparatus which can upload data to a data center when data stored in a data measuring apparatus is more than a first reference value, without a user's separate control.

An aspect of the present invention also provides a data collecting method and apparatus which can detect pilot signals transmitted from a wireless data transmitting/receiving station at predetermined time periods and reduce the power consumption of the data collecting apparatus.

An aspect of the present invention also provides a data collecting method and apparatus which can detect pilot signals transmitted from a wireless data transmitting/receiving station, control a data transmission condition, and transmit data to the wireless data transmitting/receiving station in an optimized data transmission condition.

An aspect of the present invention also provides a data collecting method and apparatus which can automatically upload data of a data measuring apparatus and recover storage space thereof, without a user's separate control, by automatically transmitting data to a wireless data transmitting/receiving station when the data measuring apparatus stores more data than a first reference value and deleting the transmitted data from a storage unit.

An aspect of the present invention also provides a data collecting method and apparatus which can reduce the power consumption of a data measuring apparatus by automatically transmitting data to a wireless data transmitting/receiving station when a data measuring apparatus stores more data than a first reference value and turning off a communication module when the transmission is completed.

According to an aspect of the present invention, there is provided a data collecting apparatus including: a measuring module measuring data and storing the measured data in a storage unit; and a communication module automatically transmitting the stored data to a wireless data transmitting/receiving station when an amount of the data stored in the storage unit is more than a first reference value.

According to another aspect of the present invention, there is provided a data collecting method including: collecting data from a data collecting apparatus and storing the collected data in a storage unit; and automatically transmitting the stored data from a communication module to a wireless data transmitting/receiving station when an amount of data stored in the storage unit is more than a first reference value.

According to another aspect of the present invention, there is provided a computer-readable recording medium storing a program for implementing the aforementioned method.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which:

FIG. 6 is a flowchart illustrating a process of collecting data according to the present invention.

DETAILED DESCRIPTION OF EMBODIMENTS

Figure 1:
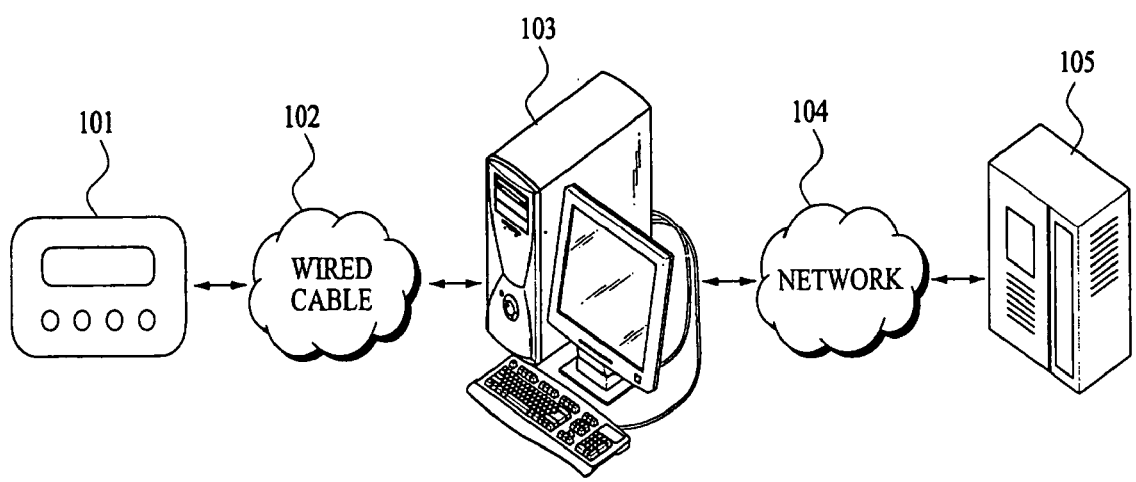
FIG. 1 is a diagram illustrating a network connection of a conventional data collecting apparatus.

Reference will now be made in detail to embodiments of the present invention, examples of which are illustrated in the accompanying drawings, wherein like reference numerals refer to the like elements throughout. The embodiments are described below in order to explain the present invention by referring to the figures.

Figure 2:
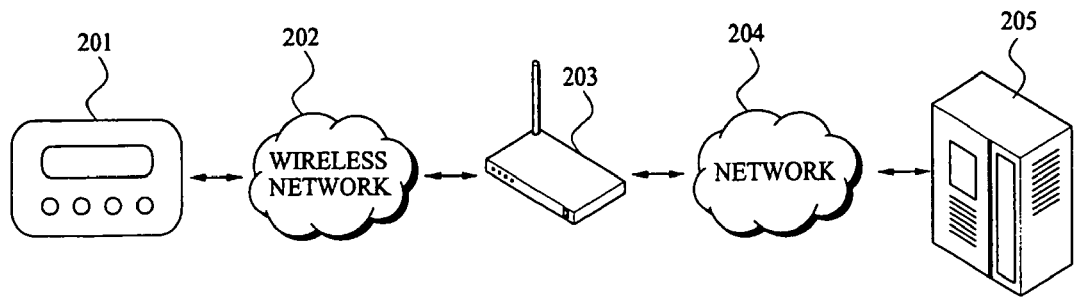
FIG. 2 is a diagram illustrating a network connection of a data collecting apparatus according to an embodiment of the present invention.

FIG. 2 is a diagram illustrating a network connection of a data collecting apparatus according to an embodiment of the present invention. A data collecting apparatus 201 is wirelessly connected to a wireless data transmitting/receiving station 203 via a wireless network 202. Also, the wireless data transmitting/receiving station 203 is connected to a data center 205 via a network 204.

The data collecting apparatus 201 of the present embodiment includes a predetermined communication module such as a Code Division Multiplex Access (CDMA) module, a Bluetooth module, Infrared Data Association (IrDA), and a wired/wireless LAN card and having a data collecting ability by including a predetermined data measuring module.

As an example, the data collecting apparatus 201 may include a biosignal measuring apparatus measuring and storing a user's biosignal, a digital camera or camcorder recording pictures or moving picture data photographed by a user, a location measuring apparatus measuring a user's location, and the like, as a data measuring apparatus.

The wireless data transmitting/receiving station 203 is configured to receive data from the data collecting apparatus and transmit the collected data to the data center 205. Accordingly, like the data collecting apparatus, the wireless data transmitting/receiving station 203 may include a communication module such as a CDMA module, a Bluetooth module, IrDA, and a wired/wireless LAN card.

The data center 205 is configured to manage data collected in the data collecting apparatus 201. Accordingly, the data center 205 may be connected to the wireless data transmitting/receiving station 203 via the wired/wireless network 204. Hereinafter, the data collecting apparatus 201 will be described in detail.

Figure 3:
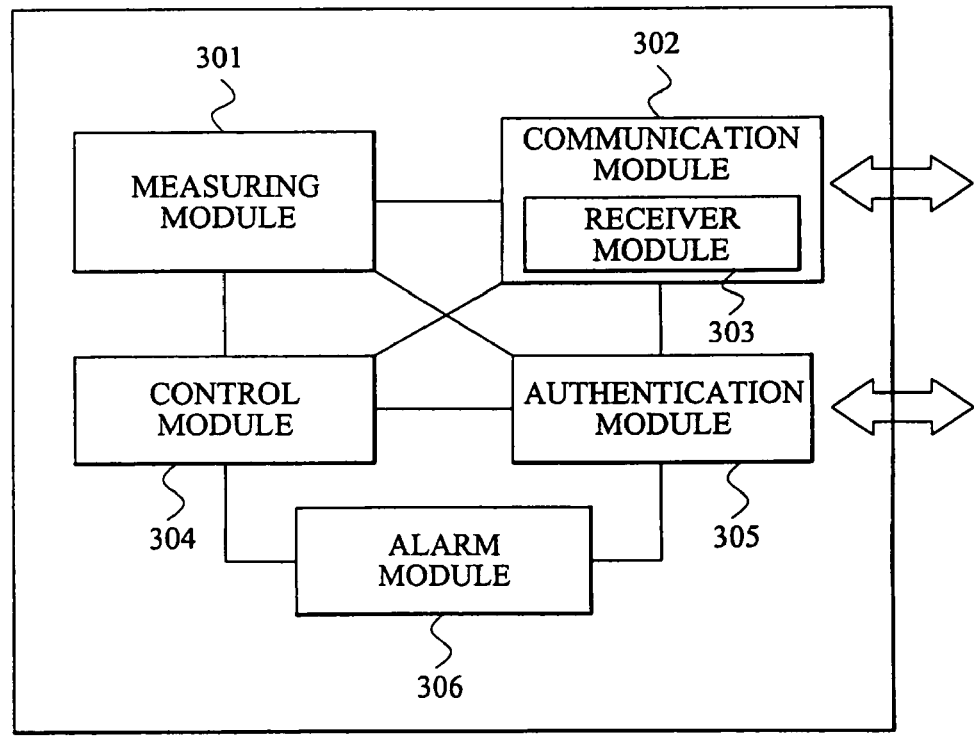
FIG. 3 is a block diagram illustrating a configuration of a data collecting apparatus according to an embodiment of the present invention.

FIG. 3 is a block diagram illustrating a configuration of a data collecting apparatus according to an embodiment of the present invention. Referring to FIG. 3, a data collecting apparatus includes a measuring module 301, a communication module 302, a control module 304, an authentication module 305, and an alarm module 306.

The measuring module 301 measures predetermined data and stores the measured data in a storage unit (not illustrated). The data are associated with a user's biosignal such as blood pressure, pulse, heart rate, the amount of motion, and the like. Also, the data includes all types of data such as location data associated with a user's location, image data, moving picture data, and the like. The measuring module 301 measures the data as described above.

In this case, when the data is received in a same state for more than predetermined time, the measuring module 301 may delete data received in the same state and store the rest of data in the storage unit.

For example, when the measuring module 301 is configured to measure a user's heart rate and the heart rate is received in the same state for more than 30 minutes, data of a section where the heart rate was received in the same state is deleted and the rest of data is stored in the storage unit. Accordingly, the capacity of the storage unit may be saved.

The communication module 302 automatically transmits the stored data to a wireless data transmitting/receiving station when an amount of the data stored in the storage unit is more than a first reference value.

When the measuring module is configured to measure the amount of motion of a user, the measuring module measures data of the amount of motion of the user for 24 hours and records the measured data in a storage unit. In this case, the communication module 302 automatically transmits the stored data of the amount of motion to a wireless data transmitting/receiving station when an amount of data stored in the storage unit is more than an amount of data corresponding to 24 hours.

In this case, the communication module 302 may include a receiver module 303 activated when an amount of data stored in the storage unit is more than the first reference value. In the above example, the receiver module 303 may be activated when an amount of data stored in the storage unit is more than an amount of data corresponding to 24 hours.

The receiver module 303 detects a pilot signal transmitted from the wireless data transmitting/receiving station. The wireless data transmitting/receiving station is installed in a predetermined location and transmits a pilot signal.

The pilot signal is a signal for detecting a location of a wireless data transmitting/receiving station for a data collecting apparatus. The pilot signal is transmitted in a predetermined range from the wireless data transmitting/receiving station according to a setting thereof.

The receiver module 303 may detect the pilot signal at predetermined time periods. This is because the power consumption of the data collection apparatus increases when the receiver module 303 constantly operates. The first time period may be set as an appropriate value according to an amount of power consumption of the receiver module 303.

Namely, according to the present invention, a receiver module detects a pilot signal per predetermined time periods. Accordingly, the power consumption of a data collecting apparatus may be reduced.

When a data collecting apparatus is positioned in a predetermined range from a wireless data transmitting/receiving station, the receiver module 303 detects a pilot signal. Also, the receiver module 303 activates the communication module 302 to transmit data stored in a storage unit to the wireless data transmitting/receiving station.

The receiver module 303 detects the strength of the pilot signal and calculates data transmission distance corresponding to the strength of the detected pilot signal. The communication module 302 may control a transmission condition of the data by referring to the calculated data transmission distance.

For example, the receiver module 303 may detect the strength of the pilot signal and calculate data transmission distance as 5.5 m. The communication module 302 may control a data transmission condition by referring to the calculated data transmission distance and transmit data in an optimized data transmission condition.

The authentication module 305 performs an authentication process via communication with the wireless data transmitting/receiving station.

In this case, the authentication module 305 may perform an authentication process by transmitting an identifier corresponding to the data collecting apparatus to the wireless data transmitting/receiving station and receiving an authentication signal therefrom.

Figures 4, 5:
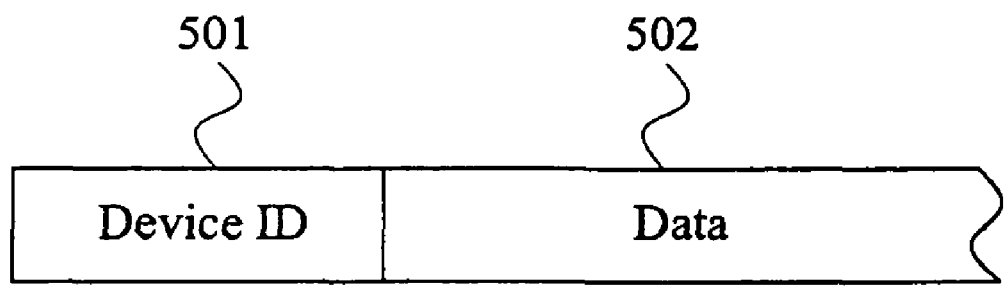
FIG. 4 is a diagram illustrating a database of a wireless data transmitting/receiving station according to an embodiment of the present invention.
FIG. 5 is a diagram illustrating data transmitted to a wireless data transmitting/receiving station according to an embodiment of the present invention.

FIG. 4 is a diagram illustrating a database of a wireless data transmitting/receiving station according to an embodiment of the present invention.

Referring to FIG. 4, a wireless data transmitting/receiving station maintains an identifier of a data collecting apparatus in a predetermined database. The identifier is for identifying the data collecting apparatus that is being managed in each wireless data transmitting/receiving station.

That is, a wireless data transmitting/receiving station maintains an identifier corresponding to a data collecting apparatus, such as identifier "1000001", identifier "1000002", and the like.

The wireless data transmitting/receiving station determines whether the identifier is recorded in a database by referring to the database illustrated in FIG. 4. When an identifier transmitted from a data collecting apparatus is recorded in the database, the wireless data transmitting/receiving station performs an authentication process by generating an authentication signal and transmitting the generated authentication signal to the communication module 302.

When the authentication process is completed, the communication module 302 transmits data stored in a storage unit to the wireless data transmitting/receiving station.

FIG. 5 is a diagram illustrating data transmitted to a wireless data transmitting/receiving station according to an embodiment of the present invention. When an authentication process is completed, a data collecting apparatus of the present invention transmits data stored in a storage unit to a wireless data transmitting/receiving station. In this case, identifier information and data may be simultaneously transmitted by transmitting a data collecting apparatus identifier 501 and data 502 to a wireless data transmitting/receiving station.

For example, the communication module 302 of the data collecting apparatus transmits the identifier 501 as "1000001", and data 502 as "amount of motion of a user stored for 24 hours", to a wireless data transmitting/receiving station.

The wireless data transmitting/receiving station transmits the received data and identifier to a data center. The data center stores the data in association with the identifier.

According to the present embodiment, when data stored in a data measuring apparatus is more than a first reference value, the data is automatically transmitted to a wireless data transmitting/receiving station with an identifier of the data measuring apparatus. Also, the wireless data transmitting/receiving station automatically transmits the received data and identifier to a data center. Accordingly, a user may upload data to the data center without the need to control the data measuring apparatus When the receipt of the data is terminated, the wireless data transmitting/receiving station transmits a signal of terminating the receipt of data to a communication module of a data collecting apparatus.

When the communication module receives the termination signal from the wireless data transmitting/receiving station, the control module 304 deletes the transmitted data from the storage unit. For example, the control module 304 deletes data of "the amount of motion of a user stored for 24 hours," which is data transmitted to the wireless data transmitting/receiving station, from the storage unit.

Namely, according to the present embodiment, when a data measuring apparatus stores more data than a first reference value, the stored data is automatically transmitted to a wireless data transmitting/receiving station. Also, the transmitted data is deleted from a storage unit. Accordingly, data uploading of the data measuring apparatus and recovery of a storage space is automatically performed.

For example, a user is an office worker and carries a data collecting apparatus for 24 hours. Also, the user leaves the office and goes home after storing data of the amount of motion corresponding to 24 hours in a storage unit of the data collecting apparatus. Also, a wireless data transmitting/receiving station is positioned adjacent to the user's home. In this case, when the user comes home and approaches an area where a pilot signal is transmitted from a wireless data transmitting/receiving station, data stored in the data collecting apparatus is automatically transmitted to the wireless data transmitting/receiving station. The transmitted data is transmitted to a data center. Accordingly, the user may upload data of his/her amount of motion to the data center without a separate uploading process.

Also, when the uploading is terminated, data of the amount of motion corresponding to 24 hours stored in the storage unit of the data collecting apparatus is deleted. Accordingly, the user may collect the amount of motion of the next day by using the data collecting apparatus without manually deleting data to recover a storage space.

In particular, when the data is associated with a user's pulse, heart rate, the amount of motion, and the like, the data does not need a user's separate control. When the data is managed in a data center, the data may be more availably used since the data is very useful Also, according to present embodiment, the control module turns off the communication module when the termination signal is received. When data stored in a storage unit is once again more than a first reference value, a receiver module is activated again. Also, when a pilot signal is detected in the receiver module, a communication module is activated again.

Accordingly, when a data measuring apparatus stores more data than a first reference value, the present embodiment automatically transmits the stored data to a wireless data transmitting/receiving station. When the transmission is completed, a communication module is turned off to reduce the power consumption of the data measuring apparatus.

Data measuring apparatuses as described above are usually carried by users. Accordingly, the data measuring apparatuses need to be manufactured in a small size and be lightweight. To make data apparatuses in a small size and lightweight and to have its power supply last longer, it is important is to reduce the power consumption.

The alarm module 306 of FIG. 3 outputs an alarm signal when an amount of the data stored in the storage unit is more than a second reference value.

The capacity of a storage unit of a data measuring apparatus is limited. Accordingly, more data may not be stored than the limited capacity. Namely, when more data is stored in the storage unit than a second reference value, the alarm module 306 of the present embodiment outputs an alarm signal to let a user know that data of the storage unit has to be uploaded. The second reference value may be set as a predetermined value by considering the capacity of the storage unit. Also, the second reference value may be larger than the first reference value.

When an alarm signal is outputted from the alarm module 306, only if a user approaches a wireless data transmitting/receiving station with the user's data collecting apparatus, the user may upload data stored in a storage unit and secure the capacity of the storage unit.

In particular, when a data measuring apparatus collects data associated with a user's biosignal, the data measuring apparatus needs an alarm function described above to continuously collect the user's biosignal.

FIG. 6 is a flowchart illustrating a process of collecting data according to the present invention.

Referring to FIG. 6, in operation S601, a wireless data transmitting/receiving station 602 transmits a pilot signal.

A data collecting apparatus 601 collects data and stores the collected data in a storage unit. Also, the data collecting apparatus 601 activates a receiver module when an amount of data stored in the storage unit is more than a first reference value.

In this instance, the data may be various types of data including data associated with a user's biosignal. When the data is received in a same state for predetermined time, the data collecting apparatus 601 may conserve storage space by deleting data received in the same state and storing the rest of data in the storage unit.

Also, when an amount of the data stored in the storage unit is more than a second reference value, the data collecting apparatus 601 may output an alarm signal to let a user know that it is necessary to recover the capacity of the storage unit.

A receiver module of the data collecting apparatus 601 may detect the pilot signal per predetermined time periods to reduce the power consumption. The receiver module activates a communication module when a pilot signal transmitted from the wireless data transmitting/receiving station is detected.

In operation S602, the data collecting apparatus 601 transmits an identifier of the data collecting apparatus to the wireless data transmitting/receiving station to perform an authentication process.

The wireless data transmitting/receiving station 602 determines whether the identifier is recorded in a database by referring to the database. When the identifier is recorded in the database, the wireless data transmitting/receiving station 602 generates an authentication signal and transmits the generated authentication signal to the data collecting apparatus 601 in operation S603.

In operation S604, after the authentication signal is received, the data collecting apparatus 601 automatically transmits the data stored in the storage unit to the wireless data transmitting/receiving station. In this instance, the data collecting apparatus 601 may automatically transmit the stored data to the wireless data transmitting/receiving station via the communication module, by detecting the strength of the pilot signal, calculating data transmission distance corresponding to the strength of the detected pilot signal, and controlling a transmission condition of the data with reference to the calculated transmission distance. This has been already described above.

The wireless data transmitting/receiving station 602 transmits the received data and identifier to a data center, and the data center stores the data in association with the identifier. Accordingly, the data center may manage data collected for each identifier of a data collecting apparatus.

In operation S605, when the receipt of the data is terminated, the wireless data transmitting/receiving station 602 transmits the termination signal to the data collecting apparatus.

When the termination signal is received, the data collecting apparatus deletes the transmitted data from the storage unit. According to the above-described embodiments embodiments, when the termination signal is received, the data collecting apparatus may turn off the communication module to reduce the power consumption.

Until now, the data collecting method according to the above-described embodiment of the present invention has been described. Technical contents described in the aforementioned embodiments may be applicable to the data collecting method of FIG. 6 as is. Accordingly, the description related thereto will be omitted.

The data collecting method according to the above-described embodiment of the present invention may be recorded in computer-readable media including program instructions to implement various operations embodied by a computer. The media may also include, alone or in combination with the program instructions, data files, data structures, and the like. The media and program instructions may be those specially designed and constructed for the purposes of the present invention, or they may be of the kind well known and available to those having skill in the computer software arts. Examples of computer-readable media include magnetic media such as hard disks, floppy disks, and magnetic tape; optical media such as CD ROM disks and DVD; magneto-optical media such as floptical disks; and hardware devices that are specially configured to store and perform program instructions, such as read-only memory (ROM), random access memory (RAM), flash memory, and the like. The media may also be a transmission medium such as optical or metallic lines, wave guides, etc. including a carrier wave transmitting signals specifying the program instructions, data structures, etc. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention.

When data stored in a data measuring apparatus is more than a first reference value, the above-described embodiments of the present invention automatically transmit the data to a wireless data transmitting/receiving station with an identifier of the data measuring apparatus. The wireless data transmitting/receiving station automatically transmits the received data and identifier to a data center. Accordingly, a user may upload data to a data center without the user's separate control.

Also, the above-described embodiment of the present invention can detect pilot signals transmitted from a wireless data transmitting/receiving station per predetermined time periods and reduce the power consumption of the data collecting apparatus.

Also, the above-described embodiment of the present invention can detect pilot signals transmitted from a wireless data transmitting/receiving station, control a data transmission condition, and transmit data to the wireless data transmitting/receiving station in an optimized data transmission condition.

Also, the above-described embodiment of the present invention can automatically upload data of a data measuring apparatus and recover a storage space thereof, without a user's separate control, by automatically transmitting data to a wireless data transmitting/receiving station when the data measuring apparatus stores more data than a first reference value and deleting the transmitted data from a storage unit.

Also, the above-described embodiment of the present invention can reduce the power consumption of a data measuring apparatus by automatically transmitting data to a wireless data transmitting/receiving station when a data measuring apparatus stores more data than a first reference value and turning off a communication module when the transmission is completed.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A portable data collecting apparatus comprising:
   a measuring module measuring data and storing the measured data in a storage unit;
   a communication module automatically transmitting the stored data to a wireless data transmitting/receiving station when an amount of the data stored in the storage unit is more than a first reference value; and
   an authentication module performing an authentication procedure through communication with the wireless data transmitting/receiving station, wherein the authentication module transmits to the wireless data transmitting/receiving station an identifier corresponding to the data collecting apparatus and receives an authentication signal therefrom, and
   the wireless data transmitting/receiving station determines whether the identifier is recorded in a database by referring to the database and, when the identifier is recorded in the database, generates the authentication signal and transmits the generated authentication signal to the communication module, thereby authorizing the transmission of the stored data from the storage unit to the wireless data transmitting/receiving station,
   wherein the measuring module, the storage unit, the communication module, and the authentication module, are all included within the portable data collecting apparatus.

2. The apparatus of claim 1, wherein:
   the communication module comprises a receiver module activated when an amount of the data stored in the storage unit is more than the first reference value, and
   the receiver module activates the communication module when a pilot signal transmitted from the wireless data transmitting/receiving station is detected.

3. The apparatus of claim 2, wherein the receiver module attempts to detect the pilot signal at predetermined time periods.

4. The apparatus of claim 2, wherein:
   the receiver module detects an intensity strength of the pilot signal and calculates a data transmission distance corresponding to the intensity strength of the detected pilot signal, and
   the communication module controls a transmission condition of the data by referring to the calculated data transmission distance.

5. The apparatus of claim 1, wherein the wireless data transmitting/receiving station transmits the received data and identifier to a data center and the data center stores the data in association with the identifier.

6. The apparatus of claim 1, further comprising a control module deleting the transmitted data from the storage unit, when the communication module receives a signal of termination of receipt of data from the wireless data transmitting/receiving station,
   wherein the wireless data transmitting/receiving station transmits the termination signal to the communication module when the receipt of the data is completed.

7. The apparatus of claim 6, wherein the control module turns off the communication module when the termination signal is received.

8. The apparatus of claim 1, wherein the measuring module, when the data is received in a same state for more than a predetermined time, deletes data received in the same state and stores the rest of data in the storage unit.

9. The apparatus of claim 1, further comprising an alarm module outputting an alarm signal when an amount of data stored in the storage unit is more than a second reference value.

10. The apparatus of claim 1, wherein the data is associated with a user's biosignal.

11. A method of collecting data, the method comprising:
    collecting data using a measuring module of a portable data collecting apparatus and storing the collected data in a storage unit; and
    automatically transmitting the stored data from a communication module to a wireless data transmitting/receiving station when an amount of data stored in the storage unit is more than a first reference value, wherein the automatically transmitting the stored data comprises;
    transmitting an identifier of the data collecting apparatus from an authentication module to the wireless data transmitting/receiving station;
    determining whether the identifier is recorded in a database by referring to the database, and when the identifier is recorded in the database, generating an authentication signal and transmitting the generated authentication signal to the data collecting apparatus via the wireless data transmitting/receiving station; and
    automatically transmitting the stored data to the wireless data transmitting/receiving station when the data collecting apparatus receives the authentication signal,
    wherein the measuring module, the storage unit, the communication module, and the authentication module, are all included within the portable data collecting apparatus.

12. The method of claim 11, wherein the automatically transmitting the stored data from a predetermined communication module to a wireless data transmitting/receiving station when an amount of data stored in the storage unit is more than a first reference value comprises:
    activating a receiver module when an amount of data stored in the storage unit is more than the first reference value; and automatically transmitting the stored data from the communication module to the wireless data transmitting/receiving station when the receiver module detects a pilot signal transmitted from the wireless data transmitting/receiving station.

13. The method of claim 12, wherein the receiver module attempts to detect the pilot signal at predetermined time periods.

14. The method of claim 12, further comprising detecting a strength of the pilot signal and calculating a data transmission distance corresponding to the strength of the detected pilot signal via the receiver module, wherein
the automatically transmitting the stored data from the communication module to the wireless data transmitting/receiving station when the receiver module detects a pilot signal transmitted from the wireless data transmitting/receiving station comprises: controlling a transmission condition of the data by referring to the calculated data transmission distance; and automatically transmitting the stored data from the communication module to the wireless data transmitting/receiving station.

15. The method of claim 11, wherein the wireless data transmitting/receiving station transmits the received data and identifier to a data center and the data center stores the data in association with the identifier.

16. The method of claim 11, further comprising:
transmitting a termination signal to the data collecting apparatus when the receipt of the data is terminated at the wireless data transmitting/receiving station; and
deleting the transmitted data from the storage unit when the data collecting apparatus receives the termination signal.

17. The method of claim 16, further comprising turning off the communication module when the data collecting apparatus receives the termination signal.

18. The method of claim 11, wherein the collecting data from a data collecting apparatus and storing the collected data in a storage unit comprises, when the data is received in a same state for more than a predetermined time, deleting data received in the same state and storing the rest of data in the storage unit.

19. The method of claim 11, further comprising outputting an alarm signal when an amount of data stored in the storage unit is more than a second reference value.

20. The method of claim 11, wherein the data is associated with a user's biosignal.

21. A non-transitory computer-readable recording medium storing a program for implementing a method of collecting data, the method comprising:
collecting data using a measuring module of a portable data collecting apparatus and storing the collected data in a storage unit; and
automatically transmitting the stored data from a communication module to a wireless data transmitting/receiving station when an amount of data stored in the storage unit is more than a first reference value, wherein the automatically transmitting the stored data comprises;
transmitting an identifier of the data collecting apparatus from an authentication module to the wireless data transmitting/receiving station;
determining whether the identifier is recorded in a database by referring to the database, and when the identifier is recorded in the database, generating an authentication signal and transmitting the generated authentication signal to the data collecting apparatus via the wireless data transmitting/receiving station; and
automatically transmitting the stored data to the wireless data transmitting/receiving station when the data collecting apparatus receives the authentication signal,
wherein the measuring module, the storage unit, the communication module, and the authentication module, are all included within the portable data collecting apparatus.

22. The apparatus of claim 1, wherein when data measured by the measuring model remains unchanged for more than a predetermined time, the measuring module deletes the data that has remained unchanged for more than the predetermined time and stores any other measured data.

23. The method of claim 11, wherein when data collected by the measuring model remains unchanged for more than a predetermined time, the measuring module deletes the data that has remained unchanged for more than the predetermined time and stores any other measured data.

* * * * *

UNITED STATES PATENT AND TRADEMARK OFFICE
CERTIFICATE OF CORRECTION

PATENT NO. : 8,188,858 B2
APPLICATION NO. : 11/372377
DATED : May 29, 2012
INVENTOR(S) : Kwang Hyeon Lee et al.

It is certified that error appears in the above-identified patent and that said Letters Patent is hereby corrected as shown below:

First page Column 1 (Inventors), Line 4, Delete "Youngin-si" and insert --Yongin-so--, thereafter Signed and Sealed this
Twenty-seventh Day of November, 2012

David J. Kappos
*Director of the United States Patent and Trademark Office*